United States Patent
Sandford et al.

(10) Patent No.: US 10,478,381 B2
(45) Date of Patent: Nov. 19, 2019

(54) MINIMIZATION OF AIR INGRESS IN SOLUTION CONTAINERS

(71) Applicant: Fenwal, Inc., Lake Zurich, IL (US)

(72) Inventors: Craig Sandford, Buffalo Grove, IL (US); Daryl Calhoun, Gurnee, IL (US); Robert Payton, Lake Zurich, IL (US)

(73) Assignee: Fenwal, Inc., Lake Zurich, IL (US)

( * ) Notice: Subject to any disclaimer, the term of this patent is extended or adjusted under 35 U.S.C. 154(b) by 962 days.

(21) Appl. No.: 14/792,744

(22) Filed: Jul. 7, 2015

(65) Prior Publication Data

US 2016/0008223 A1 Jan. 14, 2016

Related U.S. Application Data

(60) Provisional application No. 62/021,753, filed on Jul. 8, 2014.

(51) Int. Cl.
*A61J 1/16* (2006.01)
*A61M 1/02* (2006.01)

(52) U.S. Cl.
CPC .............. *A61J 1/16* (2013.01); *A61M 1/0277* (2014.02)

(58) Field of Classification Search
CPC ....... A61J 1/10; A61J 1/14; A61J 1/16; B65B 5/061; B65D 77/06; Y10S 128/24; A61M 1/0277
See application file for complete search history.

(56) References Cited

U.S. PATENT DOCUMENTS

| | | | | |
|---|---|---|---|---|
| 3,576,650 A | * | 4/1971 | Underwood et al. | B65D 65/38 206/438 |
| 4,090,374 A | * | 5/1978 | Faust | A61J 1/1462 62/341 |
| 5,017,338 A | * | 5/1991 | Surgenor | A61J 1/05 128/DIG. 24 |
| 5,383,324 A | | 1/1995 | Segers et al. | |
| 5,750,216 A | * | 5/1998 | Horino | B32B 27/08 428/34.3 |
| 5,797,881 A | * | 8/1998 | Gadot | A61M 5/148 604/131 |
| 6,468,259 B1 | | 10/2002 | Loretti et al. | |
| 6,508,800 B1 | | 1/2003 | Keilman et al. | |
| 7,875,016 B2 | | 1/2011 | Pahlberg et al. | |
| 2004/0110299 A1 | * | 6/2004 | Sivavec | G01N 1/18 436/25 |

(Continued)

*Primary Examiner* — Ariana Zimbouski
(74) *Attorney, Agent, or Firm* — Cook Alex Ltd.

(57) ABSTRACT

A medical solution packaging assembly comprising a medical solution container that houses a medical solution comprising a semi-permeable material including one or more surface that is at least partially permeable to air molecules and has low permeability to vapor molecules of the medical solution, wherein the medical solution container is configured to inflate beyond its original volume. The assembly further comprising a packaging comprising one or more surface within which the solution container resides; a compressing mechanism configured to apply external force onto at least one surface of the medical solution container or limit the volume to which the medical solution container inflates, wherein a volume of air ingress from an external environment of the medical solution container is less than that which would occur without the compressing mechanism.

18 Claims, 9 Drawing Sheets

(56) References Cited

U.S. PATENT DOCUMENTS

2007/0167107 A1* 7/2007 Petell .................. A63H 27/10
 446/220
2013/0216749 A1 8/2013 Aiba

* cited by examiner

MINIMIZATION OF AIR INGRESS IN SOLUTION CONTAINERS

CROSS REFERENCE TO RELATED APPLICATIONS

This application claims the benefit of the filing date of U.S. Provisional Application Ser. No. 62/021,753, filed Jul. 8, 2014 the entire contents being incorporated herein by reference.

FIELD OF THE DISCLOSURE

The present disclosure generally relates to optimization of storage for solution containers. More particularly, the present disclosure relates to a device that applies force to a medical solution bag or restricts the volume to which it can inflate, so that air ingress into the container is minimized during storage.

BACKGROUND

Infusion solution bags and other medical solution containers are often stored for months and even years after initial manufacture before they are ultimately put to use at a healthcare facility. It is known that during these lengthy periods of time, given the semi-permeable nature of the bag material, air enters the bag and results in a slow inflation, or ballooning, of the bag. The air ingress can be as little as none to complete inflation of the bag within six months, depending on the container material and length of period in storage.

The precise mechanism for ballooning is not well understood but it is known to interfere with bag function both in terms of causing storage difficulty and over-pressurization of the bag. Prior to their use at healthcare facilities, solution bags are removed from the manufacturer's packaging and stored temporarily while awaiting patient use or further processing. A solution bag that has inflated during storage in the manufacturer's packaging can sometimes be cumbersome to remove as well as awkward to stack and store.

Additionally, ballooning can over-pressurize the bag and in some situations impair normal solution flow during use of the bag with a patient. While some technologies that receive the solution bag have built-in pressure controllers to control the solution flow from the bag, many technologies that receive the bag do not include such features.

This known problem of air ingress has been resolved in the art in two ways: 1) incorporation of an overpouch or additional layer that surrounds the solution bag, or 2) selection of an alternate bag material that alleviates the air ingress issue.

Incorporating an overpouch or additional layer may add time, cost, and resources to the manufacturing process and using alternate bag materials with optimized permeability can potentially be cost-prohibitive in certain circumstances. Therefore, there exists a real need for a solution that addresses the air ingress problem while allowing the use of lower cost materials, including materials that could not be used on their own in the past due to the ballooning issues.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

According to an exemplary embodiment, the present disclosure is directed to a medical solution packaging assembly comprising a medical solution container that houses a medical solution comprising a semi-permeable material including one or more surface that is at least partially permeable to air molecules and has low permeability to vapor molecules of the medical solution, wherein the medical solution container is configured to inflate beyond its original volume. The assembly also comprises packaging comprising one or more surface within which the solution container resides. The assembly also comprises e compressing mechanism configured to apply external force onto at least one surface of the medical solution container or limit the volume to which the medical solution container inflates, wherein a volume of air ingress from an external environment of the medical solution container is less than that which would occur without the compressing mechanism.

According to an exemplary embodiment, the present disclosure is directed to a medical solution packaging assembly comprising a medical solution container that houses a medical solution comprising a semi-permeable material including one or more surface that is at least partially permeable to air molecules and has low permeability to vapor molecules of the solution, wherein the medical solution container is configured to inflate beyond its original volume. The assembly also comprises a compressing mechanism configured to apply external force onto at least one surface of the medical solution container or limit the volume to which the medical solution container inflates, wherein the volume of air ingress from an external environment of the medical solution container is less than that which would occur without the compressing mechanism. The compressing mechanism also includes a band or wrap configured to at least partially wrap around a surface of the solution container and exert force upon it.

According to an exemplary embodiment, the present disclosure is directed to a method of packaging an infusible medical solution container for apheresis or infusion products comprising providing packaging for transport or storage of an infusible medical solution container, wherein the packaging includes a plurality of walls and an inner open space for receiving at least one infusible medical solution container; providing a compressing mechanism that is configured to apply force onto the at least one infusible medical solution container when placed in the inner open space with the infusible medical solution container; wherein air ingress from the exterior to the interior of the medical solution container is at least partially restricted by the force applied by the compressing mechanism.

DETAILED DESCRIPTION

Air ingress leading to a ballooning effect may be driven by gas partial pressures. Gas partial pressures may underlie one mechanism for ballooning and may answer the question of why air would continue entering a solution container even when total air pressure inside the container is equal to or greater than that of outside the container.

Atmospheric pressure is approximately 760 torr and consists of the partial pressures of the atmosphere's gases. The partial pressures are approximately 593 torr for nitrogen, 159 torr for oxygen, 7 torr for argon and 1 torr for trace others. When a solution container with solution filled inside is initially manufactured at atmospheric pressure, the partial pressures of the individual gases within the container are the same as the outside atmospheric partial pressures. However, by virtue of the moisture from the solution entering the air within the container as water vapor, a partial pressure for water vapor will develop in the air above the solution. At 20° C., the partial pressure of water vapor is about 17.5 torr and may decrease the total pressure of the remaining gases by that amount. Therefore, when the solution container is sealed, this may result in initial partial pressures of 579 torr for nitrogen and 155 torr for oxygen inside the container. This produces a driving pressure of 14 torr for nitrogen and 5 torr for oxygen to migrate into the container. This migration may continue to occur until the partial gas pressures inside and outside the container have equalized, a point at which the estimated total pressure is 777.5 torr or approximately 0.34 psi internal pressure, although the numbers may vary slightly according to factors such as temperature, surface area of the internal air bubble in contact with the container, internal container pressure, wall thickness or gas permeability of the container, external pressure, altitude, and humidity.

The equation $P_I = P_E + P_{H2O}$ approximately describes the point at which gas ingress will stop, where $P_I$ is total internal air pressure within the container, $P_E$ is the total pressure of the external air surrounding the container, and $P_{H2O}$ is the partial pressure of water vapor within the container. Attempts have been made to slow the rate of air ingress with use of alternate material that decreases air permeability, or to equalize water partial pressure inside and outside the container by employing an overpouch having higher water vapor barrier properties than that of the container. The present embodiments address the problem by increasing the initial $P_I$ value so that gas ingress may be discouraged from the start.

The manipulation of the $P_I$ value can be accomplished in several ways. A strategically designed packaging insert can be used to restrict the volume to which a solution container can inflate, or it can apply force onto the container. Alternatively or additionally, a band, clip, or clamp that applies force onto the container may also elevate $P_I$ from the outset. Since pressure is equal to force divided by the surface area over which the force is applied, the force applied by the packaging insert, band, clip, or clamp may translate into an applied pressure that changes the $P_I$ value.

Figure 1:
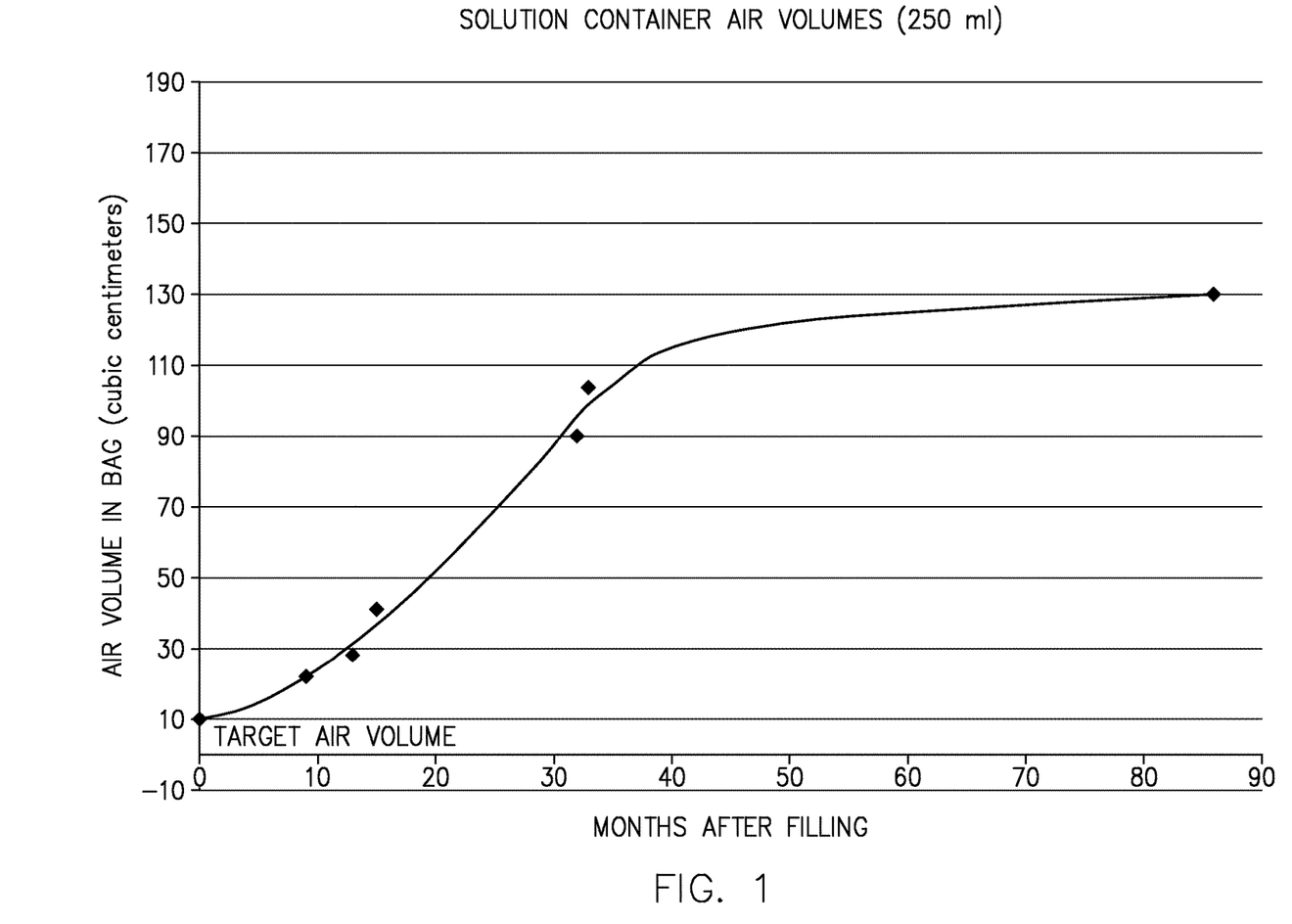
FIG. 1 shows a graph demonstrating natural air ingress in a free-standing container as a function of time after initial manufacture of filled solution container, according to an exemplary embodiment.

FIG. 1 shows a graph demonstrating natural air ingress for one type of free-standing container (e.g., no restriction mechanism, no insert, etc.) as a function of time after initial manufacture of filled solution container. Air volumes were measured by extracting air from the container with a syringe. Target air volume refers to the amount of air initially in the container prior to any air ingress. It is the ideal amount of air that would remain in the container at the time of actual use of the solution. It should be appreciated that an air pressure differential between the inside and outside of the container may not immediately ensue even as air initially ingresses into the container, due to the fact that the container may not be filled to capacity.

Figure 2:
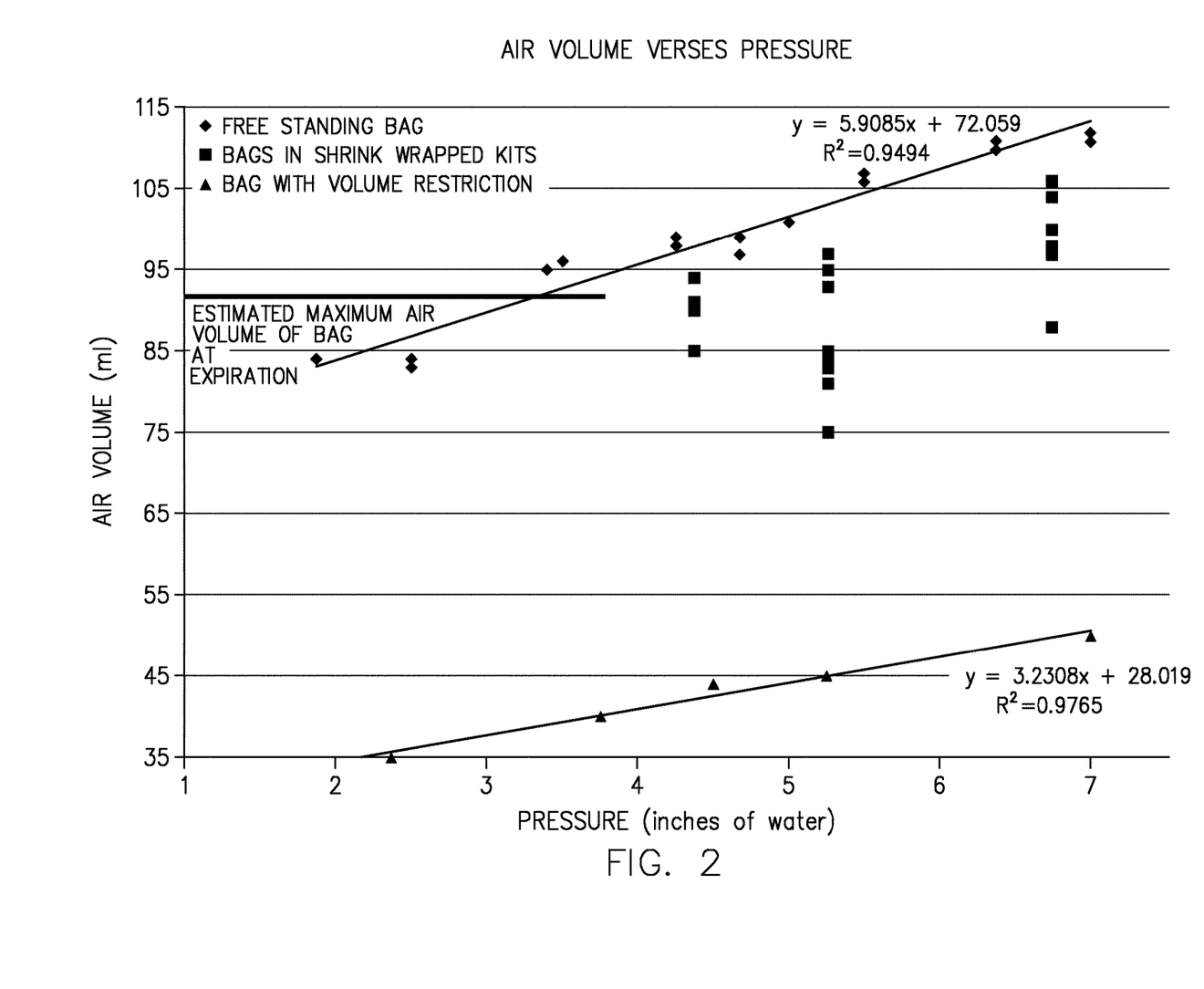
FIG. 2 shows a graph demonstrating the effect restricting the container's ability to inflate has on the amount of air that will enter the container with an applied external force, according to an exemplary embodiment.

FIG. 2 shows the effect restricting the container's ability to inflate may have on the amount of air that can migrate into the container. The data points of FIG. 2 simulate the air volume that would be required to inflate the container to a given pressure. The diamond data points represent free-standing containers into which air was manually pumped until the air inside reached a maximum volume of about 110 mL. The internal air pressure at this maximum volume was 7 inches of water (approximately 13.1 torr). The square data points represent containers whose volumes were restricted by shrink-wrap upon their surface. Inside these containers, the manually pumped air reached maximum volumes of between 87 and 106 mL, with a pressure of 6.7 inches of water (approximately 12.6 torr). Finally, the triangular data points represent containers that ax were restricted within a confined space in their packaging. For these containers, the manually pumped air reached a maximum volume of around 50 mL, with a pressure of 7 inches of water (approximately 13.1 torr). This graph allows for the determination of how much air volume would be expected to enter a container to attain a certain pressure, given varying packaging constraints. The graph also demonstrates that packaging constraints may decrease the volume of air ingress it takes to reach a certain pressure than the volume it takes for a free-standing container.

The graph of FIG. 2 also provides an indirect method of determining the pressure that a particular packaging is exerting on the container. For a free-standing container with air manually injected into the container, it will contain approximately 72 mL of air within the container and have zero air pressure differential between the inside and outside of the container, as determined by the curve fit equation y=5.9085x+72.059 for the diamond data point graph in FIG. 2. It should be noted that the 72 mL of air is greater than the 10 mL target air volume from FIG. 1 and yet the air pressure differential is zero in both cases. As noted above, this is due to the container not having been filled to full capacity before internal air pressure begins to increase. Similarly the air volume within a free-standing bag for a given internal air pressure can be determined from this equation. Air fill volumes at a given internal air pressure can also be determined for bags constrained by packaging geometry. The air volume for bags constrained by packaging can be expected to be lower than the air volume in a free-standing (unrestrained) bag with the same internal air pressure. When the bag is removed from the packaging constraints, the pressure in the bag will drop. The resulting pressure can be estimated using the aforementioned curve fit equation to calculate the new pressure for the measured air volume in the now free-standing bag.

Either a volume constraint placed on the container or force applied externally onto the container will decrease the volume of air that will enter the container to attain partial pressure equilibrium. It has been shown in practice in the industry that solution containers are stored in temperatures as high as 41° C. and as low as 11° C. At these temperatures, the vapor pressures of water are 57 torr and 10 torr, respectively. If relative humidity in the atmosphere is zero, which is true on certain days and in certain dry areas, the amount of air ingress can produce, for a free-standing container, an internal container pressure as high as 57 torr greater than surrounding pressure. FIGS. 3-8 portray several embodiments of the invention that counteract this pressure.

Figure 3:
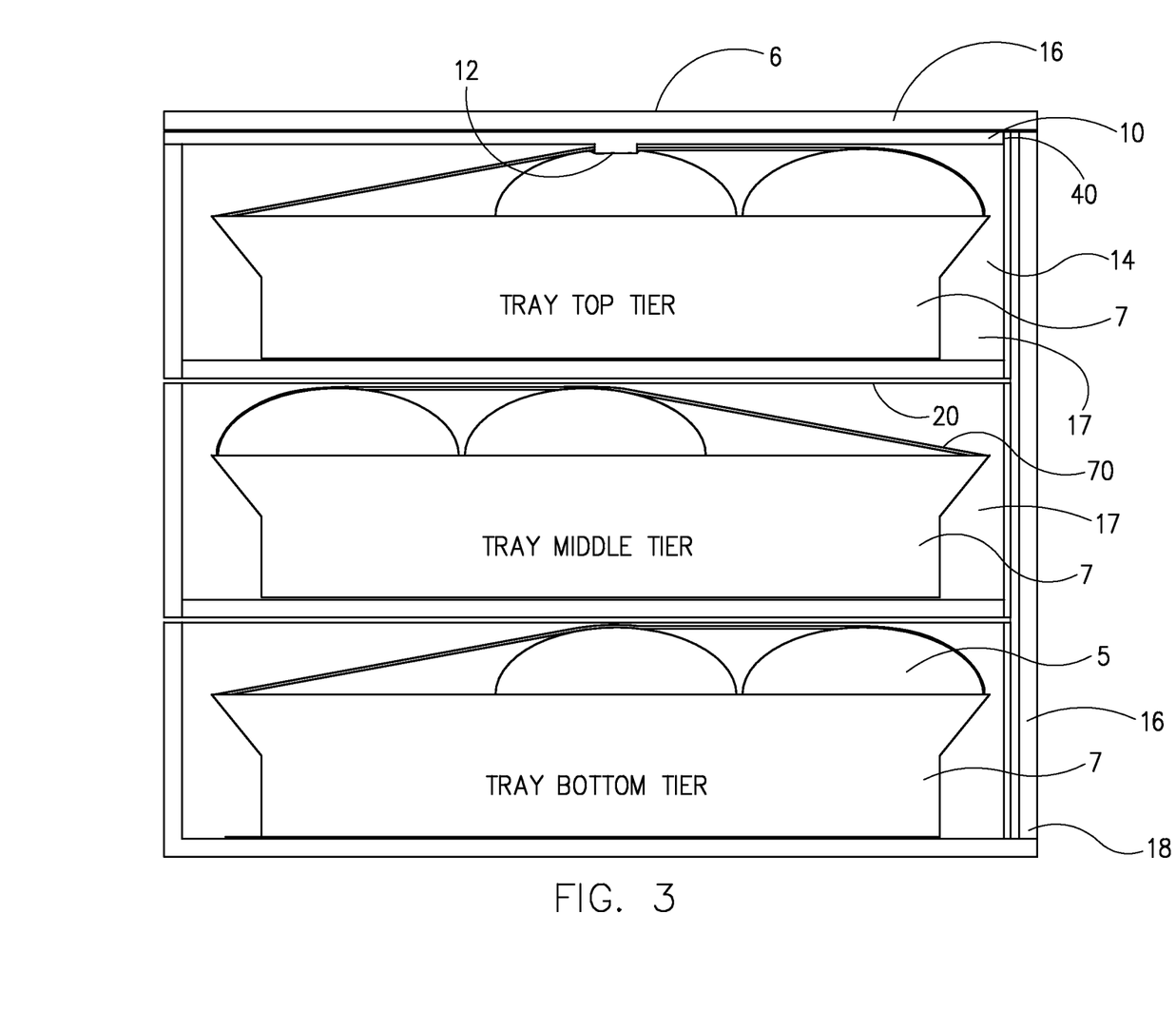
FIG. 3 is a view of packaged solution containers and an example packaging configuration that constricts volume or applies force to the container, according to an exemplary embodiment.

Referring to FIG. 3, solution (e.g., saline, anticoagulant, blood product additive solution, infusion solutions, enteral feedings solutions, etc.) containers 5 are packaged in trays 7 in a tiered configuration. A package insert 10 may be placed between the solution containers 5 and the wall (e.g., lid, surface, ceiling, etc.) 16 within an open space 17 of the packaging (e.g., container, assembly, etc.) 18, such that the package insert 10 may restrict the volume to which a solution container 5 may inflate or may apply force to the solution container 5 such that internal pressure within the solution container 5 may become elevated. The application of force can be accentuated by a further protrusion 12 of the package insert 10 that makes contact with the solution container 5 and compresses it. If desired, a package insert 10 can be placed at each tier of the packaging 18, between the solution container 5 and the floor (e.g., base, bottom, etc.) 20 of the tier above it. The width of the package insert 10 can be increased or decreased, depending on the magnitude of applied force desired.

Figure 4:
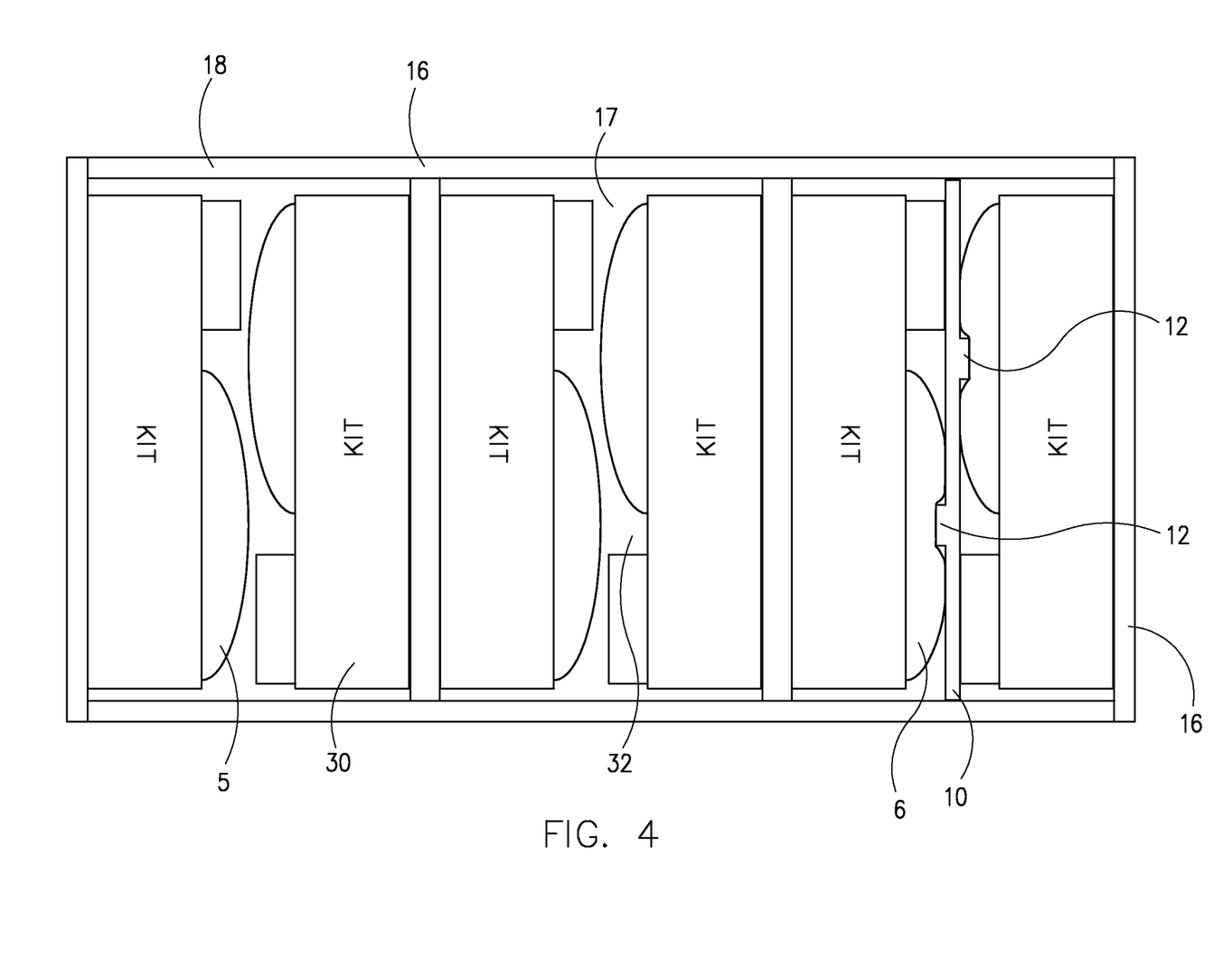
FIG. 4 is a view of another package configuration that constricts volume or applies force to the container with a package insert in-between, according to an exemplary embodiment.

Referring to FIG. 4, solution containers 5 are packaged in a staggered orientation, with the volume of a solution container 5 of one kit 30 fitting into the groove or open space 32 of an opposing kit. A package insert 10 may be placed between two kits 30 such that it forms a single plane that applies force onto both solution containers 5 simultaneously or restricts volume simultaneously. A protrusion 12 may or may not be added to the insert 10, and the width of the package insert 10 can be increased or decreased, depending on the magnitude of applied force desired.

Figure 5A:
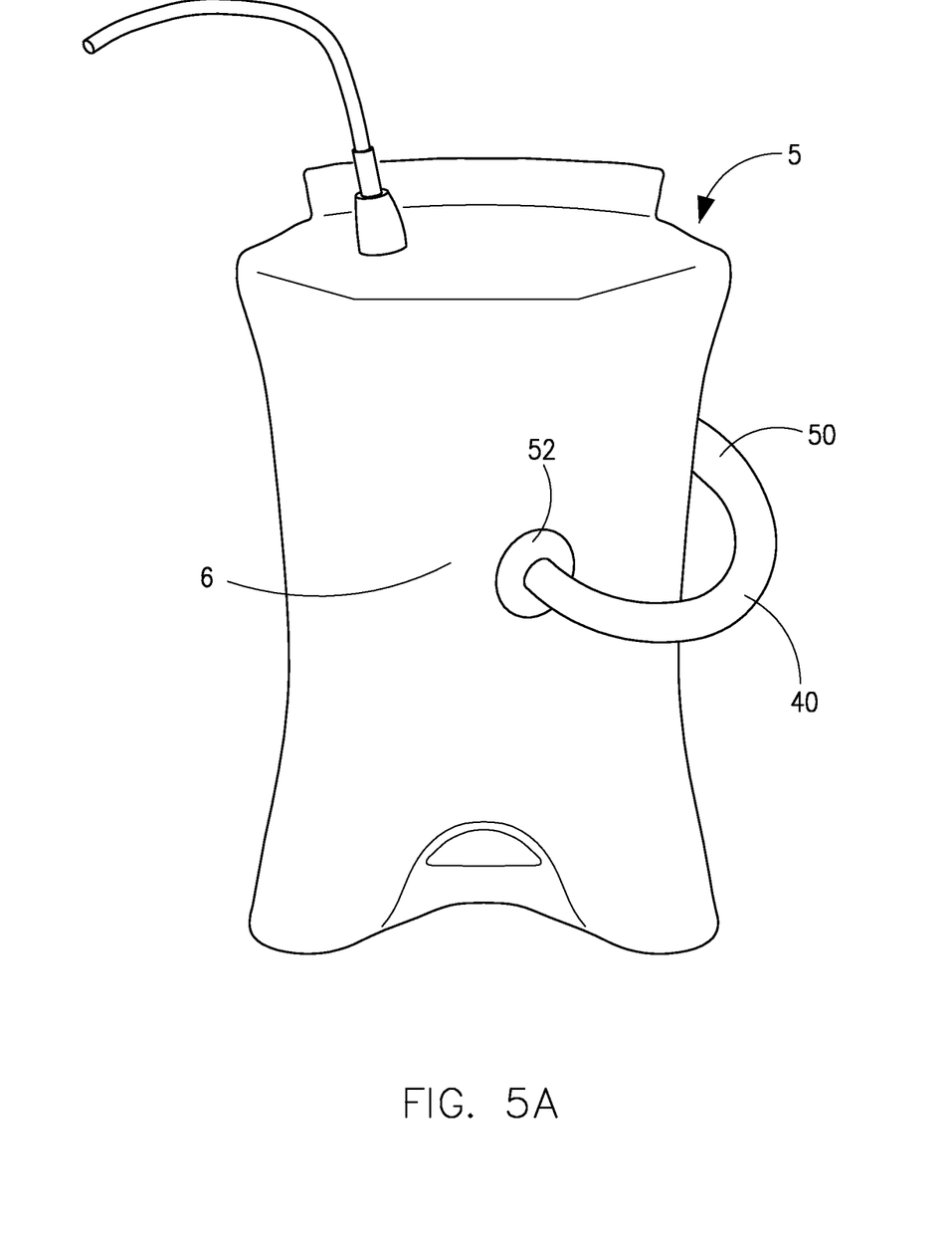
FIG. 5A is a front view of a solution container having a clamp applied against opposing surfaces of the container, according to an exemplary embodiment.
Figure 5B:
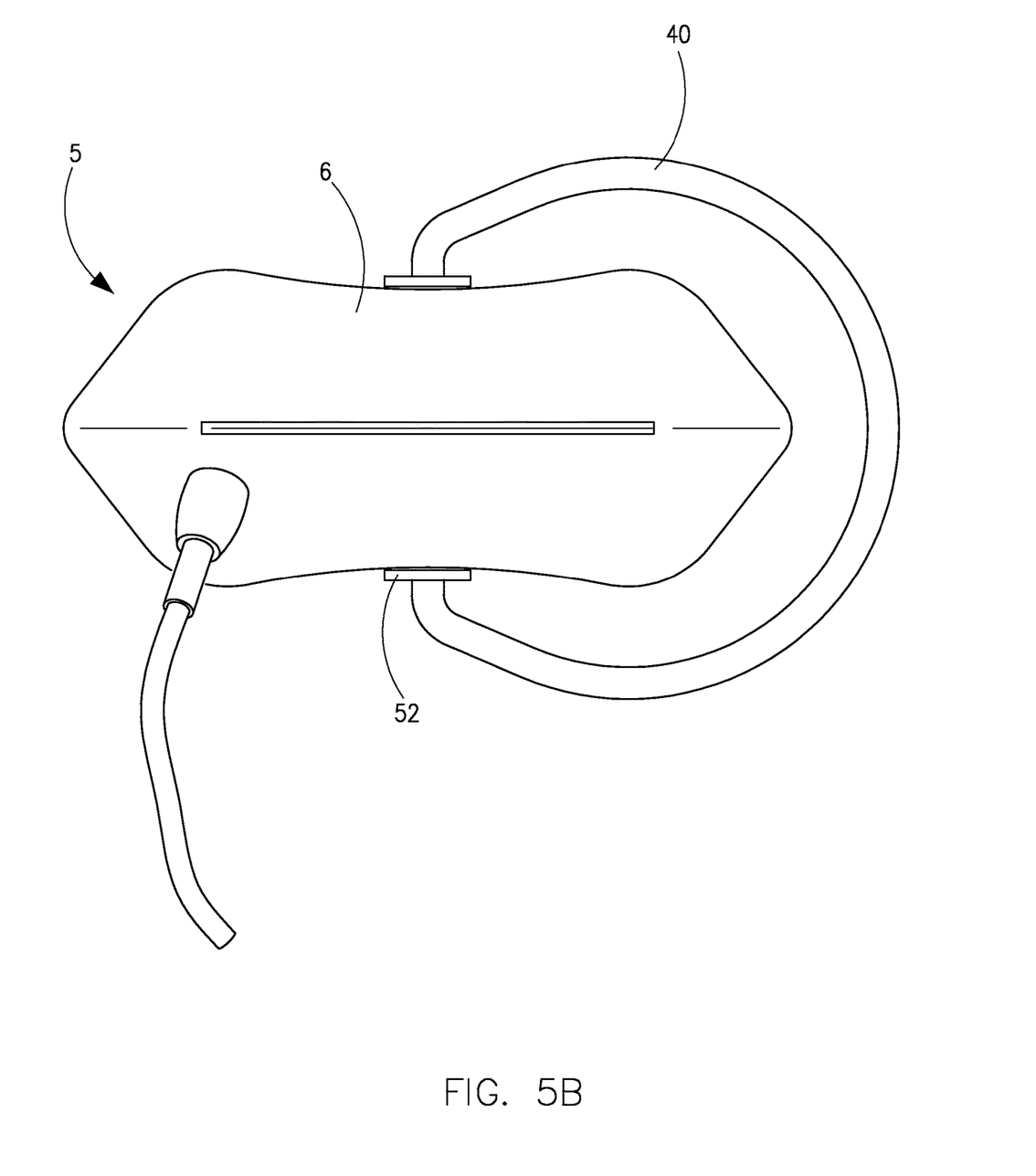
FIG. 5B a top cross-sectional view of FIG. 5A, according to an exemplary embodiment.

In lieu of or in conjunction with package inserts 10 compressing mechanisms 40 may accompany the solution containers 5. FIGS. 5A and 5B show a generally C-shaped clamp 50 that applies force to the surface 6 of the solution container 5 such that $P_I$ is increased. The contact surface area of the face 52 of the clamp abutting the surface 6 of the solution container 5 should be as small as possible without risk of puncturing the container material. The reason for this single and sole concentrated point of application is that pressure equals force divided by area, and therefore, with the same amount of force, pressure is maximized by minimizing surface area of the force.

Figure 6:
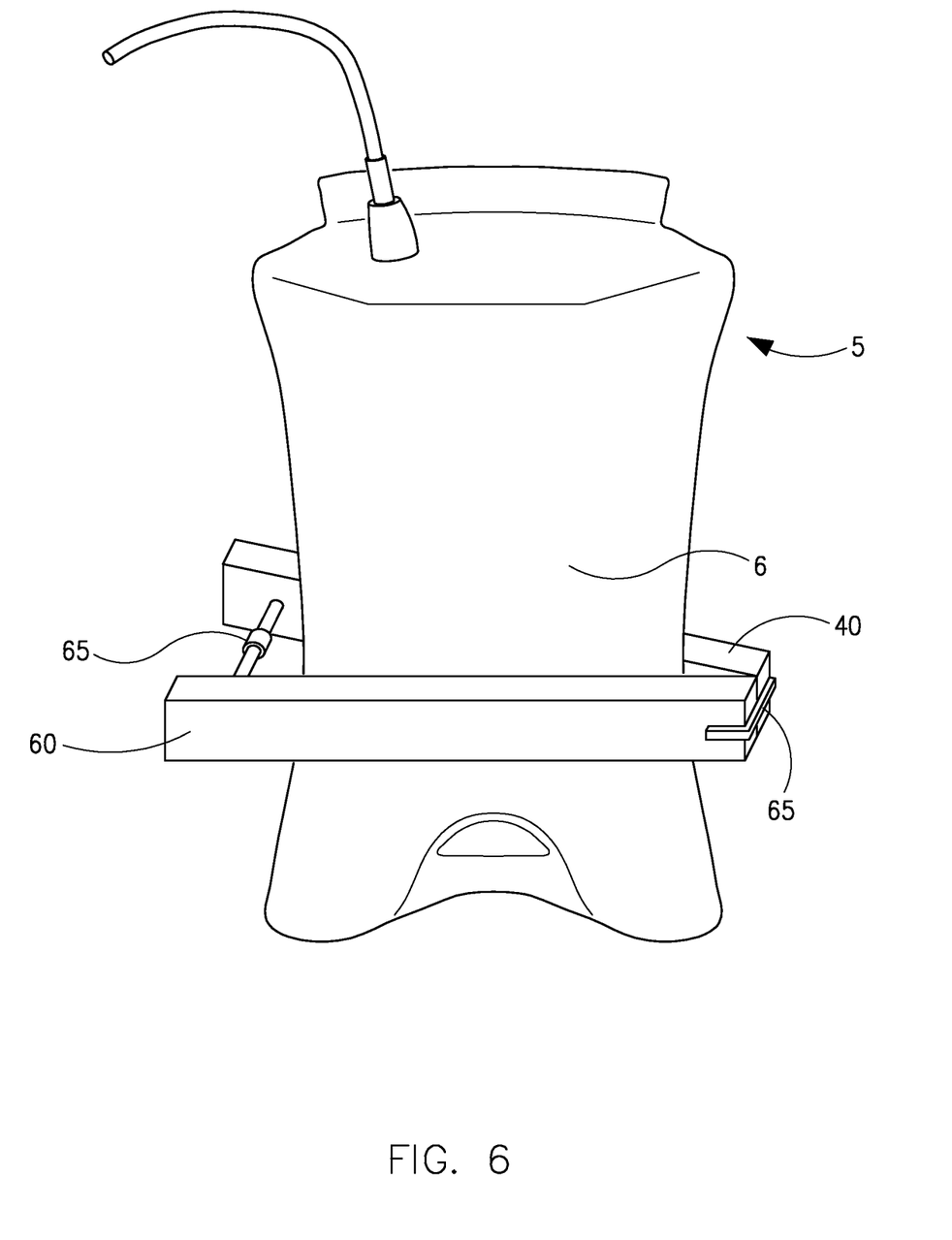
FIG. 6 is a front view of a solution container having a clip or clamp disposed transversely across the length of the container and exerting force onto the face of the container, according to an exemplary embodiment.
Figure 7:
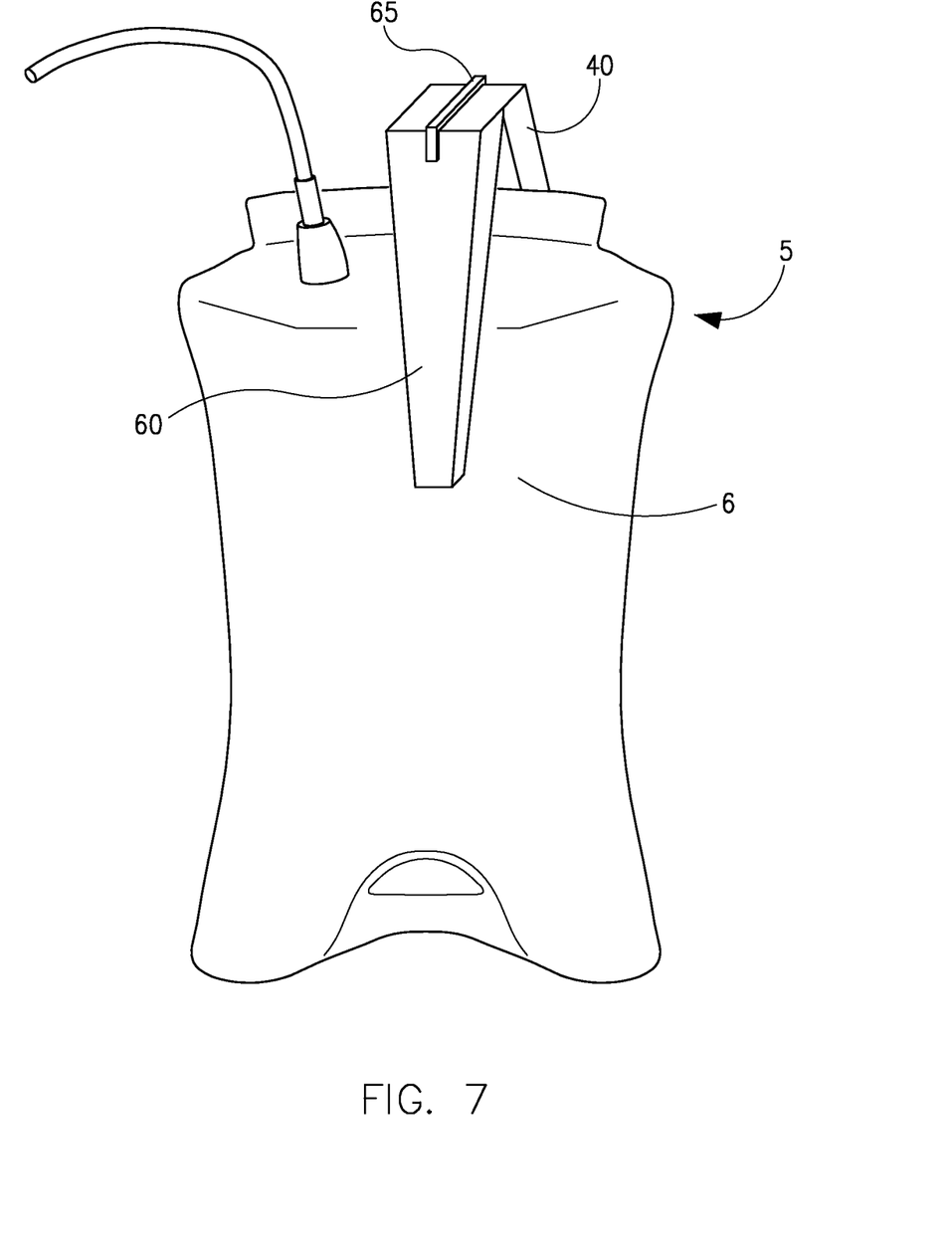
FIG. 7 is a front view of a solution container having a clip or clamp disposed longitudinally along the length of the container and exerting force onto the surface of the container, according to an exemplary embodiment.

FIG. 6 depicts an alternate embodiment in which a clip or clamp 60 is used to exert force onto the surface 6 of the container 5 and thereby increase initial $P_I$. The clip or clamp 60 may be disposed transversely across the length of the solution container 5 and may be locked by a suitable clasp, spring hinge, or locking mechanism 65. FIG. 7 depicts the clip or clamp 60 disposed longitudinally along the length of the solution container 5 and may exert force onto the surface 6 of the container 5 through a suitable spring hinge or other clamping or locking mechanism 65.

Figure 8:
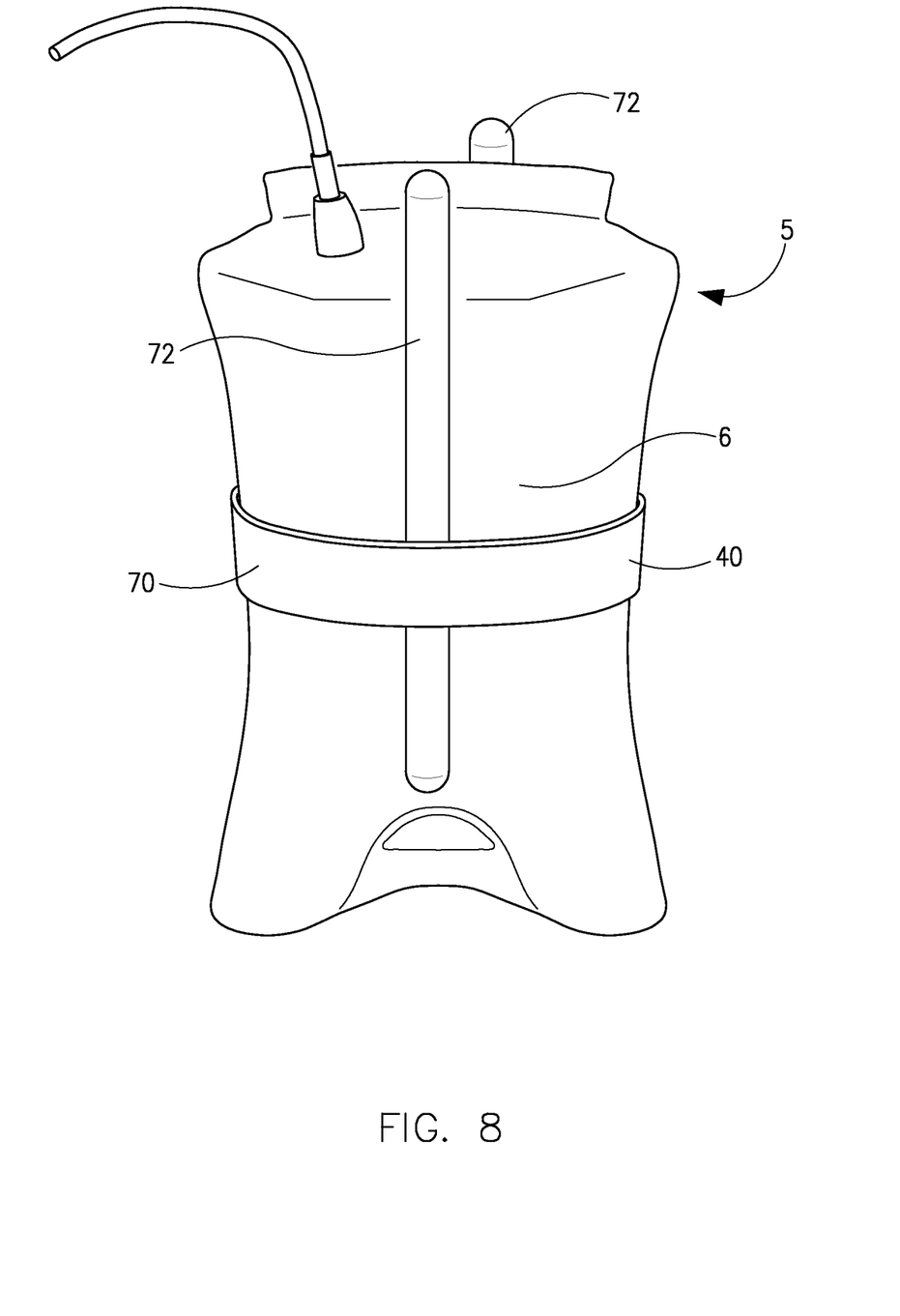
FIG. 8 is a front view of a solution container having a supporting frame and a band or wrap wrapped at least partially around the container, according to an exemplary embodiment.

FIG. 8 depicts an alternate embodiment in which a band or wrap 70 may be wrapped at least partially on or around the surface 6 of the solution container 5. A frame 72 disposed along the length or width of the solution container 5 may be present to prevent shape distortion of the container 5. The frame 72 may be of varying length, width, or height to accommodate the differing structural weaknesses of different solution containers 5. Any number of frames 72 may be used, including against one or more sides of the solution container surface 6. The material of the band or wrap 70 may be elastomeric or shrink material that would maintain tension and exert force upon the solution container surface 6 for the duration of storage. The band or wrap 70 may completely encircle the surface 6 of the solution container 5 in exerting force. The band or wrap 70 may also attach the solution container 5 to a tray 7 or insert 1 that is part of the packaging, thereby serving the dual functions of increasing the internal solution container pressure $P_I$ as well as securely affixing the solution container 5 within a desired location inside protective packaging to facilitate transport of the container 5.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A medical solution packaging assembly comprising:
   a medical solution container that houses a medical solution, the medical solution container comprising a semipermeable material including one or more surface that is at least partially permeable to air molecules and has low permeability to vapor molecules of the medical solution, wherein the medical solution container is configured to inflate beyond its original volume; and
   a compressing mechanism having a single and sole concentrated point of application configured to apply external force onto at least one surface of the medical solution container or limit the volume to which the medical solution container inflates, wherein a volume of air ingress from an external environment of the medical solution container is less than that which would occur without the compressing mechanism.

2. The medical solution packaging assembly of claim 1, further comprising a packaging having one or more surface within which the medical solution container resides, and wherein the compressing mechanism includes at least one insert disposed between the medical solution container and a surface of the packaging.

3. The medical solution packaging assembly of claim 1, wherein the external force applied by the compressing mechanism onto the medical solution container results in a pressure value in the range of 10 to 57 torr.

4. The medical solution packaging assembly of claim 2, wherein the insert includes a protrusion defining the single and sole concentrated point of application that contacts the medical solution container.

5. The medical solution packaging assembly of claim 1, further comprising a packaging having one or more surface within which the medical solution container resides, and wherein multiple tiers of medical solution containers are disposed within the packaging.

6. The medical solution packaging assembly of claim 5, wherein the medical solution containers are in a staggered orientation and one or more insert is disposed between two medical solution containers.

7. The medical solution packaging assembly of claim 1, wherein the external force applied by the compressing mechanism onto the medical solution container results in a pressure value in the range of 10 to 57 torr.

8. The medical solution packaging assembly of claim 1, wherein the medical solution container comprises at least one of anticoagulant, saline, blood product additive solution, enteral solution, and parenteral solution used for apheresis or infusion procedures.

9. A method of packaging an infusible medical solution container for apheresis or infusion products comprising:
providing packaging for transport or storage of an infusible medical solution container, wherein the packaging includes a plurality of walls and an inner open space for receiving at least one infusible medical solution container; and
providing a compressing mechanism having a single and sole concentrated point of application that is configured to apply force onto the at least one infusible medical solution container when placed in the inner open space with the infusible medical solution container, wherein air ingress from the exterior to the interior of the medical solution container is at least partially restricted by the force applied by the compressing mechanism.

10. The method of claim 9, wherein the compressing mechanism includes a protrusion defining the single and sole concentrated point of application configured to apply force onto the infusible medical solution container.

11. The method of claim 9, wherein the force applied by the compressing mechanism onto the medical solution container is in the range of 10 to 57 torr.

12. The method of claim 9, wherein multiple tiers of medical solution containers are disposed within the inner open space.

13. The method of claim 12, wherein the medical solution containers are in a staggered orientation and at least one compressing mechanism disposed between two of the medical solution containers.

14. The method of claim 9, wherein the infusible medical solution container comprises at least one of anticoagulant, saline, blood product additive solution, enteral solution and parenteral solution.

15. The medical solution packaging assembly of claim 1, wherein a portion of the medical solution container is positioned between an aligned pair of contact surface areas of the compressing mechanism.

16. The medical solution packaging assembly of claim 5, wherein
the compressing mechanism includes opposing surfaces, and
each of said opposing surfaces includes a protrusion that contacts a different one of two of said medical solution containers.

17. The medical solution packaging assembly of claim 16, wherein the protrusions of the opposing surfaces of the compressing mechanism are misaligned.

18. The medical solution packaging assembly of claim 5, wherein
each medical solution container is at least partially positioned within a kit defining a groove, and
each medical solution container is oriented so as to fit into the groove of an adjacent kit.

* * * * *